(12) United States Patent
Min et al.

(10) Patent No.: US 9,834,753 B2
(45) Date of Patent: Dec. 5, 2017

(54) METHOD FOR PRODUCING NATURAL KILLER CELLS, NATURAL KILLER CELLS PRODUCED THEREBY, AND COMPOSITION FOR TREATING CANCERS AND INFECTIOUS DISEASES CONTAINING THE SAME

(71) Applicants: Mogam Biotechnology Institute, Gyeonggi-do (KR); Green Cross Labcell, Gyeonggi-do (KR)

(72) Inventors: Bokyung Min, Gyeonggi-do (KR); Hana Choi, Gyeonggi-do (KR); Okjae Lim, Gyeonggi-do (KR); Jung Hyun Her, Gyeonggi-do (KR); Sangmi Kang, Gyeonggi-do (KR); Eun-Kyoung Lee, Gyeonggi-do (KR); Hyejin Chung, Gyeonggi-do (KR); Yu Kyeong Hwang, Gyeonggi-do (KR)

(73) Assignees: GREEN CROSS LABCELL, Gyeonggi-Do (KR); MOGAM BIOTECHNOLOGY INSTITUTE, Gyeonggi-Do (KR)

( * ) Notice: Subject to any disclaimer, the term of this patent is extended or adjusted under 35 U.S.C. 154(b) by 565 days.

(21) Appl. No.: 14/367,813

(22) PCT Filed: Dec. 18, 2012

(86) PCT No.: PCT/KR2012/011114
§ 371 (c)(1),
(2) Date: Jun. 20, 2014

(87) PCT Pub. No.: WO2013/094988
PCT Pub. Date: Jun. 27, 2013

(65) Prior Publication Data
US 2015/0118207 A1  Apr. 30, 2015

(30) Foreign Application Priority Data
Dec. 22, 2011 (KR) .................. 10-2011-0140361

(51) Int. Cl.
| *C12N 5/00* | (2006.01) |
| *C12N 5/02* | (2006.01) |
| *C12N 5/18* | (2006.01) |
| *C12N 5/0783* | (2010.01) |
| *A61K 35/17* | (2015.01) |
| *A61K 38/38* | (2006.01) |

(52) U.S. Cl.
CPC ............ *C12N 5/0646* (2013.01); *A61K 35/17* (2013.01); *A61K 38/38* (2013.01); *C12N 2501/2302* (2013.01); *C12N 2501/515* (2013.01)

(58) Field of Classification Search
None
See application file for complete search history.

(56) References Cited

U.S. PATENT DOCUMENTS

| 5,882,650 A  * | 3/1999 | Ennis ................. C07K 14/005 424/184.1 |
| 9,062,287 B2 * | 6/2015 | Ideno .................. C12N 5/0646 |
| 2013/0011376 A1* | 1/2013 | Peled .................. A61K 31/455 424/93.71 |
| 2014/0050710 A1* | 2/2014 | Villalba Gonzalez ............ C12N 5/0646 424/93.71 |

FOREIGN PATENT DOCUMENTS

| KR | 10-2008-0008060 A | 1/2008 |
| KR | 10-2010-0011586 A | 2/2010 |
| KR | 10-1035556 B1 | 5/2011 |
| KR | 10-2011-0132618 A | 12/2011 |
| KR | 10-1133185 B1 | 4/2012 |
| WO | WO 9705239 * | 2/1997 |
| WO | WO 9732970 * | 9/1997 |

(Continued)

OTHER PUBLICATIONS

Berg, M., et al., "Clinical Grade Ex Vivo-Expanded Human Natural Killer Cells Upregulate Activating Receptors and Death Receptor Ligands and Have Enhanced Cytolytic Activity against Tumor Cells", "Cytotherapy", 2009, pp. 341-355, vol. 11, No. 3.
Castriconi, R., et al., "Human NK cell infusions prolong survival of metastatic human neuroblastoma-bearing NOD/scid mice", "Cancer Immunol Immunother", Apr. 11, 2007, pp. 1733-1742, vol. 56.
Dewan, M., et al., "Role of natural killer cells in hormone-independent rapid tumor formation and spontaneous metastasis of breast cancer cells in vivo", "Breast Cancer Res Treat", Oct. 26, 2006, pp. 267-275, vol. 104.

(Continued)

*Primary Examiner* — Michail Belyavskyi
(74) *Attorney, Agent, or Firm* — Hultquist, PLLC; Steven J. Hultquist

(57) ABSTRACT

The present invention relates to a method for producing natural killer cells (hereinafter, referred to as "NK cells"), NK cells produced thereby, and a composition for treating cancers and infectious diseases containing the same. The present invention provides a method for producing NK cells, which maintain high cytotoxicity and cell viability to exhibit high therapeutic effects against cancers and infectious diseases and can be cultured ex vivo at high efficiency and high concentration. In addition, a culture method which maintains cell concentration at a constant level is used for the production of NK cells, and thus the overgrowth of the cells can be prevented so that the cells can be maintained at an optimal state. Particularly, even when the cells are thawed after freezing, the function of the cells is not impaired, and the NK cells can maintain high cell viability and cytotoxicity. Thus, the NK cells can be easily stored and supplied in a liquid or frozen state without needing an additional treatment process.

9 Claims, 10 Drawing Sheets

(56) References Cited

FOREIGN PATENT DOCUMENTS

| WO | WO 2005007116 | * 12/2009 |
| WO | 2010110734 A1 | 9/2010 |

OTHER PUBLICATIONS

Fujisaki, H., et al., "Expansion of Highly Cytotoxic Human Natural Killer Cells for Cancer Cell Therapy", "Cancer Res", Apr. 21, 2009, pp. 4010-4017, vol. 69.

Gong, W., et al., "Ex vivo expansion of natural killer cells with high cytotoxicity by K562 cells modified to co-express major histocompatibility complex class I chain-related protein A, 4-1BB ligand, and interleukin-15", "Tissue Antigens", Dec. 2010, pp. 467-475, vol. 76.

Goodier, M., et al., "Lipopolysaccharide Stimulates the Proliferation of Human CD56+1CD3- NK Cells: A Regulatory Role of Monocytes and IL-101", "The Journal of Immunology", 2000, pp. 139-147, vol. 165.

Miller, J., et al., "Role of Monocytes in the Expansion of Human Activated Natural Killer Cells", "Blood", Nov. 1, 1992, pp. 2221-2229, vol. 80, No. 9.

North, J., et al., "Tumor-Primed Human Natural Killer Cells Lyse NK-Resistant Tumor Targets: Evidence of a Two-Stage Process in Resting NK Cell Activation", "The Journal of Immunology", 2007, pp. 85-94, vol. 178.

* cited by examiner

METHOD FOR PRODUCING NATURAL KILLER CELLS, NATURAL KILLER CELLS PRODUCED THEREBY, AND COMPOSITION FOR TREATING CANCERS AND INFECTIOUS DISEASES CONTAINING THE SAME

CROSS-REFERENCE TO RELATED APPLICATIONS

This application is a U.S. national phase under the provisions of 35 U.S.C. §371 of International Patent Application No. PCT/KR12/11114 filed Dec. 18, 2012, which in turn claims priority of Korean Patent Application No. 10-2011-0140361 filed Dec. 22, 2011. The disclosures of such international patent application and Korean priority patent application are hereby incorporated herein by reference in their respective entireties, for all purposes.

TECHNICAL FIELD

The present invention relates to a method for producing natural killer cells (hereinafter, referred to as "NK cells"), NK cells produced thereby, and a composition for treating cancers and infectious diseases containing the same.

BACKGROUND ART

For cancer treatment, various treatment methods, including surgery, radiotherapy and chemotherapy, have been developed and used. However, in the case of particular cancers and patients, these treatment methods are difficult to apply, and there is a high possibility of recurrence.

Thus, immunotherapy utilizing the immune function of patients has received increasing attention and is based on the removal of cancers by the complex interactions between immune cells having various functions. Immune cells that directly remove cancer cells include NK cells and cytotoxic T lymphocytes (CTLs), and that present antigens to these effector cells include dendritic cells (DCs) or B cells. Other examples include helper T cells (Th cells), regulatory T cells (Treg cells) and the like, which secrete various cytokines. Among these immune cells, NK cells are recognized as the most rapidly effective and efficient immune cells.

NK cells are lymphocytes that account for about 10% of blood cells and play an important role in immune responses. NK cells have various functions, and particularly have the ability to kill cancer cells or cells infected with external pathogenic bacteria, and thus function to remove cancer cells, or cells developing into cancers.

Most NK cells are normally present in the body in an inactivated state, but in order to use NK cells for therapeutic purposes, NK cells need to be activated. Thus, studies on the activation of NK cells from normal blood or the inactivated blood of patients have been actively conducted.

The high cytotoxicity of NK cells, achieved by activating NK cells ex vivo, demonstrated the possibility of NK cells for immune cell therapy. It was reported that NK cells activated ex vivo have the rapeutic effects on various cancers, particularly blood cancer such as leukemia, when they are administered after allogenic bone marrow transplantation (*Blood Cells Molecules & Disease*, 33: p 261-266, 2004). However, the distinct therapeutic effects of NK cells on solid cancers other than blood cancer have not yet been clinically proven. Specifically, it was reported that the administration of NK cells before the formation of cancers can interfere with the engraftment of cancers (*Cancer Immunol. Immunother.*, 56(11): p 1733-1742, 2007), but this treatment model does not appear to be suitable. In addition, it was reported that intraperitoneal administration of NK cells in animal tests inhibited the growth of breast cells, but it is unclear whether this inhibitory effect is attributable to NK cells (*Breast Cancer Res. Treatment*, 104(3): p 267-275, 2007).

Meanwhile, despite the possibility of NK cells as therapeutic agents for cancers or infectious diseases, the number of NK cells present in vivo is not large, and thus there is required a technology of producing large amounts of NK cells while maintaining efficiency sufficient for therapeutic purposes. However, NK cells are not sufficiently cultured and expanded in vitro. Thus, a technology for culturing and expanding NK cells at useful levels has received attention, and many studies thereon have been conducted, but the study results are still not clinically applicable.

There have been studies on the culture of NK cells not only using IL-2, which has been in T-cell proliferation/activity, but also IL-15 (*J. Immunol.*, 167(6): p 3129-3138, 2001; Blood, 106(1): p 158-166, 2005, KR2009-0121694A), OKT-3 antibody (*Experimental Hematol.*, 29(1): p 104-113, 2001) which stimulates CD3, and LPS (*J. Immunol.*, 165(1): p 139-147, 2000). However, such studies have merely found a modification of the use of IL-2 and a new proliferator, but did not suggest an epochal method for proliferation. It is generally known that, when NK cells are cultured using IL-2 or other cytokines or chemicals, the number of NK cells is increased only by about 3-10 times the initial number of NK cells.

Some researchers reported that NK cells were expanded using cancer cell lines as feeder cells. It was reported that the use of the leukemia cell line CTV-1 showed little or no improvement in proliferation (*J. Immunol.*, 178(1): p 85-94, 2007) and that culture using EBV-LCL for 21 days increased the cell number by an average of about 490 folds (*Cytotherapy*, 11(3): p 341-355, 2009). Also, culture of NK cells for 3 weeks using artificial APC (antigen-presenting cell) obtained by expressing 4-1BBL and membrane-bound IL-15 in the K562 cells increased the NK cell number by an average of 227 folds, and high cytotoxicity appeared in vitro and in vivo, but limited proliferation caused by cell death was shown (*Cancer Res.*, 69(9): p 4010-4017, 2009). Recently, there was a reported that culture of NK cells for 3 weeks in the K562 cell line transfected with MICA, 4-1BBL and IL-15 increased the NK cell number by an average of 350 folds (Tissue Antigens, 76(6): p 467-475, 2010), and there was a report that, when NK cells were cultured for 2 weeks using the K562 cell line transfected with membrane-bound IL-21 while they were stimulated at 7-day intervals, the cell number was increased by an average of 21,000 folds. However, the methods unsuitable for guaranteeing safety important for clinical application were used, because all cancer cell lines were used. In addition, because specific cancer cells are used as feeder cells, the resulting NK cells have priming specificity for the specific cancer cells.

Cells obtained by enrichment of NK cells from peripheral blood leukocytes (PBLs) without the isolation of NK cells have low cytotoxicity compared to pure NK cells, and contain T-cells that recognize self and non-self cells by autologous MHC molecules. Thus, the cells are limited to autologous transplantation, as long as T-cells are not removed. Recently, there have been developed a method comprising NK cells isolation step, and expanding the isolated NK cells with suitable stimulation using feeder cells, and a method of selectively expanding NK cells using whole PBL or peripheral blood mononuclear cells (PBMCs).

In addition, there was reported a method for culturing NK cells, which comprises a process of culturing NK cells using a medium containing anti-CD3 antibody and interleukin protein in the presence of peripheral blood leukocytes (KR 10-2010-0011586 A).

The general expansion process for allogeneic application starts with two sequential steps of magnetic depletion of CD3+ T cells and enrichment of CD56+ NK cells. In order to stimulate NK cell proliferation, irradiated feeder cells such as PBMCs [Cytotherapy 12: 750-763, 2010], Epstein-Barr virus-transformed lymphoblastoid cell lines (EBV-LCLs) [Cytotherapy 11: 341-55, 2009] are often used. Irradiated feeder cells stimulate NK cells through both humoral factors and direct cell-to-cell contact [Blood 80: 2221-2229, 1992].

In the present invention, we established a simplified and efficient method for the large-scale expansion and activation of NK cells from healthy volunteers for clinical use. After a single step of magnetic depletion of CD3+ T cells, the depleted PBMCs were stimulated and expanded with irradiated autologous PBMCs repeatedly in the presence of OKT3 and IL-2, resulting in a highly pure population of CD3-CD16+CD56+ NK cells which is desired for allogeneic purpose.

Meanwhile, albumin is one of proteins constituting the basic substance of cell and has the lowest molecular weight among simple proteins present in nature. Albumin is generally known to be used as a preservative for biological formulations, but the use of albumin to increase the stability of NK cells has not yet been reported.

As described above, a variety of methods for culturing NK cells have been described, but there is still an urgent need for a technology which can safely and stably culture and expanding a sufficient number of NK cells for application to immune cell therapy using a clinically friendly method and allows the produced NK cells to be stably stored for a long period of time and to be supplied when required. Particularly, in order to use living NK cells for therapeutic purposes, it is required to overcome the shortcoming of the NK cells in that the period in which the activity thereof is maintained (that is, availability period) is only several days. Thus, there is an urgent demand for a technology which can significantly improve the utilization of immune cells by culturing and producing NK cells, freeze-storing the produced NK cells, and thawing and providing the stored cells when required.

DISCLOSURE OF INVENTION

It is an object of the present invention to provide a method for producing large amounts of cytotoxic NK cells within a short period of time by efficiently and safely culturing and proliferating NK cells in a clinical-friendly way.

Another object of the present invention is to provide a composition containing NK cells having improved long-term storage stability and a pharmaceutical formulation comprising the same. Particularly, the composition according to the present invention may be provided as a frozen product and maintain high cell viability and cytotoxicity of the NK cells even when it is thawed.

NK cells produced according to the method of the present invention and a composition comprising the same can be effectively used for treatment of cancers and infectious diseases.

BEST MODE FOR CARRYING OUT THE INVENTION

Figure 1:
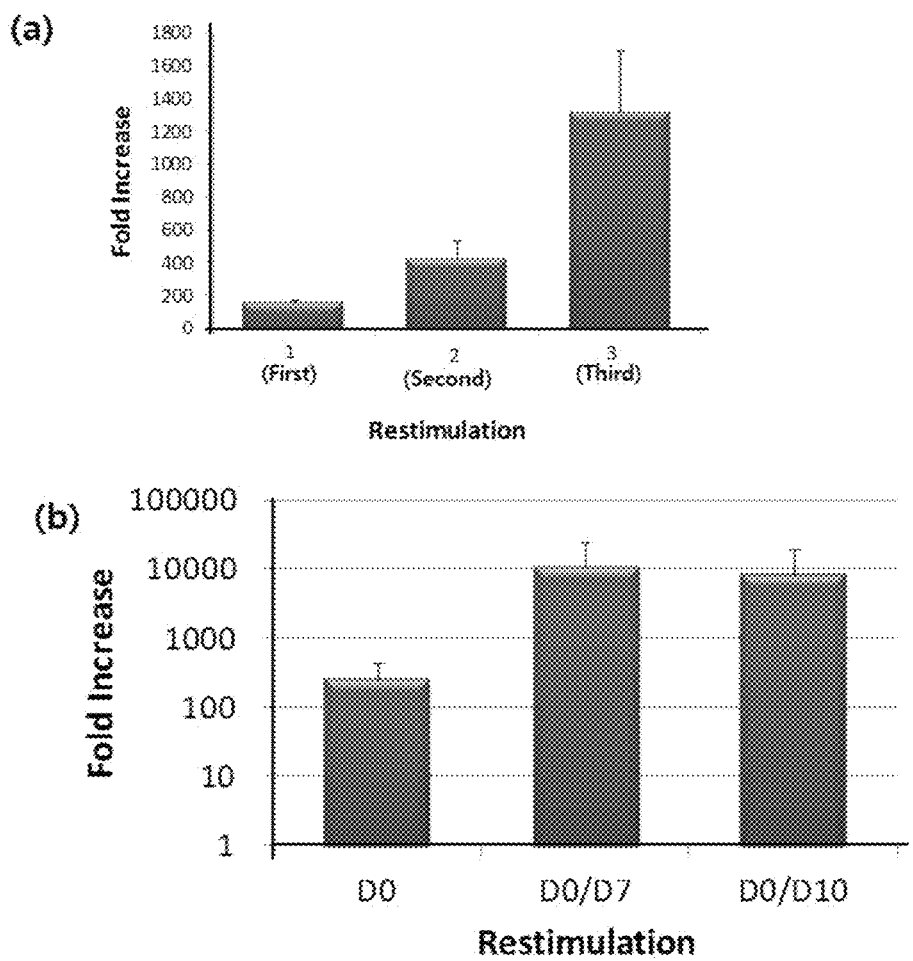
FIG. 1 shows the change in proliferation of NK cells by re-stimulation with feeder cells. (a) shows the change in proliferation rate of NK cells according to the number of re-stimulations. (a), once: application of stimulation once at day 0; twice: application of stimulation twice at days 0 and 7; and three times: application of stimulation three times at days 0, 7 and 14. (b) shows the change in proliferation rate of NK cells according to the time point of application of re-stimulation, wherein D0: application of stimulation once at day 0; D0/D7: application of stimulation twice at days 0 and 7; and D0/D10: application of stimulation twice at days 0 and 10.

Unless defined otherwise, all technical and scientific terms used herein have the same meaning as commonly understood by one of ordinary skill in the art to which the invention pertains. Generally, the nomenclatures used herein are well known and are commonly employed in the art.

A method for producing NK cells according to the present invention comprises;
  stimulating T cell-depleted mononuclear cells with anti-CD3 antibody and feeder cells in a cytokine-containing medium, and carrying out stationary culture for several days to stimulate cell-cell contact, carrying out stationary or suspension culture of NK cells in a reactor while maintaining the cell concentration and the cytokine concentration at constant levels.

In order to obtain an increased amount of NK cells, the stimulation and stationary culture may be repeated before the next stationary or suspension culture. NK cells produced by the method of the present invention maintain high cell viability and cytotoxicity to exhibit high therapeutic effects against cancers and infectious diseases and can be cultured ex vivo at high efficiency and high concentration.

In the present invention, stationary culture following initial stimulation is performed for about 2-15 days, preferably 5-10 days, and stationary culture following re-stimulation is performed for about 2-7 days, preferably 3-5 days.

After completion of the stationary culture, the cells are preferably stationary or suspension-cultured in an incubator while the concentration of cytokine is maintained at a constant level.

The method for producing NK cells according to the present invention may, for example, comprise the steps of:
  (i) isolating peripheral blood leukocytes and NK cells from human peripheral blood;
  (ii) adding the isolated NK cells to a medium containing anti-CD3 antibody and cytokine, stimulating the NK cells by addition of feeder cells, and carrying out stationary culture for 2-15 days, preferably 5-10 days to stimulate cell-cell contact;
  (iii) after completion of stationary culture in step (ii), re-stimulating the cells by addition of cytokine, anti-CD3 antibody and feeder cells, and carrying out stationary culture for 2-7 days, preferably 3-5 days, to stimulate cell-cell contact;
  (iv) after completion of the stationary culture, adding a medium containing cytokine and the like required for stationary or suspension culture, and carrying out stationary or suspension culture while maintaining cell and cytokine concentration at constant levels.

In the method for producing NK cells, step (iii) of re-stimulating the cells and carrying out stationary culture may be repeated once or more. The method of the present invention may further comprise, before step (ii), a step of preparing feeder cells.

As used herein, the term "stationary culture" means culturing cells in an incubator in a stationary state without agitation or shaking, and as used herein, the term "suspension culture" means culturing cells in a suspended state by aeration or agitation without attaching the cells to the bottom or side of the reactor.

Examples of a reactor which can be used for stationary culture in the present invention include, but are not limited to, flasks, T-flasks, disposable cell culture bags and the like. Examples of a reactor which can be used for suspension culture in the present invention include, but are not limited to, shaking flasks, shaking incubators, fermentors, T-flasks, disposable cell culture bags and the like. In addition, any bioreactor may be used which is suitable for achieving the object of the present invention and can be easily selected by a person skilled in the art to which the present invention pertains.

Moreover, the reactor for stationary culture and suspension culture may be the same or different. For example, when the reactor for stationary culture and the reactor for suspension culture are the same, stationary culture is completed and then a medium containing necessary nutrient components such as cytokine may additionally be supplied to the same reactor, followed by suspension culture. When different reactors are used, after completion of stationary culture, the cultured cells may be transferred into the reactor for suspension culture.

Examples of the reactor for suspension culture include, but are not limited to, a wave bioreactor (GE Healthcare), a single-use bioreactor (SUB; Thermo Fisher), a single-use XDR bioreactor (Xcellerex), a cell culture bag (Nipro), a PBS series cell incubator (PBS Biotech) (see WO 07/111, 677A, WO 08/133,845A, and WO 09/132,192A), a cell culture bag (Fujimori), a disposable shake flasks (Erlenmeyer) and so on. Particularly, a PBS series cell incubator (PBS Biotech) is preferred.

As used herein, the term "feeder cells" refers to cells which do not have the ability to divide and proliferate, but have metabolic activity, and thus produce various metabolic products assisting in the proliferation of target NK cells. Examples of feeder cells that may be used in the present invention include, but are not limited to, animal cell lines introduced with genes, peripheral blood leukocytes (PBL) treated with various cytokines or compounds, autologous or allogeneic peripheral blood leukocytes (PBL), T-cells, B-cells, monocytes and the like. Preferably, autologous peripheral blood monocytes may be used. In addition, other feeder cells known in the art may be used as long as they coincide with the object of the present invention.

The autologous peripheral blood monocytes that are used as feeder cells may be used in an inactivated state in order to ensure safety. For inactivation, a conventional method known in the art may be used. For example, irradiation with gamma-rays may be used. The inactivated feeder cells include isolated T-cells. The method that uses feeder cells as described in the present invention is a method of expanding NK cells after isolation and is advantageous in that only pure NK cells continuously proliferate.

"Anti-CD3 antibody" in the present invention is an antibody that binds specifically to a CD3 antigen, a molecule binding specifically to a T cell receptor (TCR) to form an antibody recognition complex, in which the CD3 molecule binds to TCR to transfer an antigen recognition signal into a cell. As the anti-CD3 antibody, any antibody may be used without limitation in the present invention, as long as it has the property of binding to CD3. The anti-CD3 antibody is preferably selected from the group consisting of OKT3, UCHT1, and HIT3a, but is not limited thereto.

In the present invention, cytokine that may be included in the medium is preferably one or more selected from among interleukins. As used herein, the term "interleukins" collectively refers to biologically active proteins which are produced by immune cells such as lymphocytes, monocytes or macrophages. An interleukin that may be used in the present invention is one or more selected from the group consisting of interleukin-2 (IL-2), interleukin-12 (IL-12), interleukin-15 (IL-15), interleukin-18 (IL-18) and interleukin-21 (IL-21). Particularly, IL-2 is preferably used, but is not limited. In addition, other cytokines known to those skilled in the art may also be used without limitation, as long as they coincide with the object of the present invention.

In the present invention, the anti-CD3 antibody is used for stationary culture and suspension culture, and the concentration of anti-CD3 antibody in medium is 0.1-1,000 ng/ml, preferably 1-100 ng/ml, and more preferably 5-20 ng/ml, and the concentration of cytokine in medium is 10-2,000 IU, preferably 100-1,000 IU, and more preferably about 200-700 IU.

As used herein, the term "stimulation" means inducing the proliferation of NK cells by adding feeder cells or the like thereto, and anti-CD3 antibody together with feeder cells may also be used for stimulation.

As used herein, the term "re-stimulation" means re-inducing the proliferation of NK cells again by adding feeder cells and/or anti-CD3 antibody thereto after a certain time of culture.

In the present invention, a medium for use in the production of NK cells may be a conventional medium for animal cell culture, such as CellGro medium (Cellgenix), AIM-V medium, RIMI-1640 medium or X-VIVO20 medium. This medium for animal cell culture may, if necessary, contain one or more components selected from among NK cells isolated from human peripheral blood, peripheral blood monocytes, anti-CD3 antibodies and interleukins.

Particularly, in the method for producing NK cells according to the present invention, in order to maintain cell concentration and cytokine concentration at constant levels, the concentrations of cytokine and cells in a medium can be measured at regular intervals of time, and based on the measurements, cytokine-containing medium may be provided according to the cell concentration and the cytokine concentration.

In addition, the medium for culture may contain serum, plasma or an additional proliferation factor that supports the proliferation of lymphocytes. Serum or plasma that is added to the medium is not specifically limited and may be a commercial product derived from an animal. More preferably, human autologous serum or plasma is used. For example, as known to those skilled in the art, it is possible to use either a combination of cytokines that induce the proliferation of lymphocytes from peripheral blood monocytes or lectins stimulates the proliferation of lymphocytes.

NK cells produced according to the method of the present invention may be provided as a therapeutic composition using a suitable excipient and additive. This composition may be administered to a patient in need of treatment, thereby achieving therapeutic effects.

Particularly, when albumin was added to a composition containing NK cells produced by the method of the present invention, the long-term storage stability, cytotoxicity and cell viability of NK cells could be greatly increased. The amount of albumin that is added to the composition of the present invention is not specifically limited, but albumin may be added in an amount of 0.1-5 wt %, and preferably 0.5-2 wt %, based on the total weight of the composition of the present invention.

In addition, when a culture method for production of NK cells, which maintains cell concentration at a constant level, is used, the overgrowth of the cells can be prevented so that the cells can be maintained at an optimal state. Particularly, even when the cells are thawed after freezing, the function of the cells is not impaired, and the NK cells can maintain high cell viability and cytotoxicity. Thus, the NK cells can be easily stored and supplied in a liquid or frozen state without needing an additional treatment process.

NK cells produced by the method of the present invention and a composition containing the same may be used for treatment of cancers and infectious diseases. NK cells produced by the method of the present invention may be applied to all types of cancers, including solid cancer and blood cancer. As used herein, the term "solid cancer" refers to mass-type cancer formed in an organ, unlike blood cancer. Cancers developed in most of organs correspond to solid cancers. Cancers which can be treated using NK cells of the present invention are not limited, and preferred examples thereof include, but are not limited to, stomach cancer, liver cancer, lung cancer, colorectal cancer, breast cancer, prostate cancer, ovarian cancer, pancreatic cancer, cervical cancer, thyroid cancer, laryngeal cancer, acute myeloid leukemia, brain cancer, neuroblastoma, retinoblastoma, head and neck cancer, salivary gland cancer, lymphoma and so on. As used herein, the term "infectious diseases" is means to include all diseases which are caused by infection with viruses or pathogenic bacteria and can be infected through respiratory organ, blood or skin contact. Non-limiting examples of such infectious diseases include, but are not limited to, hepatitis B, hepatitis C, human papilloma virus (HPV) infection, cytomegalovirus infection, viral respiratory disease, influenza and so on.

EXAMPLE

Hereinafter, the present invention will be described in further detail with reference to examples. It will be obvious to a person having ordinary skill in the art that these examples are illustrative purposes only and are not to be construed to limit the scope of the present invention.

Example 1: Culture of NK Cells by Repeated Stimulation (Re-Stimulation) with Feeder Cells and Evaluation of Characteristics (1) Culture of NK Cells by Repeated Stimulation with Feeder Cells Peripheral blood mononuclear cells (PBMC) collected from healthy donors were dispensed into a vial and frozen in liquid nitrogen. One frozen PBMC vial was thawed and transferred into a 50 mL tube, and the cells were suspended in 20 mL of PBS (phosphate buffered saline) containing 1 vol % FBS (fetal serum bovine) or autoplasma and were centrifuged at 1200 rpm at 4° C. for 10 minutes.

The PBMC pellets were suspended in 10 mL MACS running buffer, and the cells were counted by trypan blue staining. For preparation of PBMC feeder cells and depletion of CD3, $5 \times 10^7$ cells were transferred into each of 50 mL fresh tubes and centrifuged at 1200 rpm at 4° C. for 10 minutes.

PBMC feeder cells were prepared by suspending the pellets in 10 mL of 1 vol % autoplasma-containing CellGro medium (Cellgenix), followed by irradiation with 2000 cGy in a gamma-ray irradiator.

To obtain CD3-depleted cells, 400 μL of running buffer and 100 μL of CD3 magnetic beads (Miltenyi Biotech) were added to $5 \times 10^7$ cell pellets and allowed to react at 4° C. for 20 minutes. The reaction material was washed with 20 mL of MACS running buffer, and then centrifuged at 1200 rpm at 4° C. for 10 minutes and suspended in 2 mL of MACS running buffer. The cells were separated from the suspension using a CS column (Miltenyi Biotech, 130-041-305) equipped with VarioMACS (Miltenyi Biotech), and the column was washed to reach a final volume of 20 mL, thereby recovering the cells.

The cells were counted by trypan blue staining, and $1 \times 10^7$ cells were dispensed into 50 mL fresh tubes and centrifuged at 1200 rpm at 4° C. for 10 minutes. The cell pellets were suspended in 10 mL of CellGro medium (Cellgenix) containing 1 vol % autoplasma.

For bag culture, 500 IU of IL-2 and 10 ng/mL of OKT-3 were added to a tube containing PBMC feeder cells. CellGro medium (Cellgenix) containing 10 mL of PBMC feeder cells, 10 mL of NK cells and 10 mL of 1 vol % autoplasma was added to Nipro 350 bag (Nipro) and subjected to stationary culture in an incubator at 37° C. for 5 days. Herein, the Nipro 350 bag was folded 6 cm from the edge and 5 cm from the bottom so as to reach an area of about 70 cm$^2$ and used in stationary culture. For flask culture, the same composition as that in the bag culture was used, and culture was performed in a 12-well well plate using CellGro medium containing 0.5 mL of PBMC feeder cells, 0.5 mL of NK cells and 0.5 mL of 1 vol % autoplasma under the same conditions as above. Herein, the 12-well plate had an area of 3.5-3.8 cm$^2$.

At 5 days of culture, the cells were counted, diluted to about $2 \times 10^5$ cells/mL with CellGro medium (Cellgenix) containing 500 IU of IL-2 (Proleukin) and 1 vol % autoplasma and were subjected to stationary culture in a suitable incubator. Herein, the cell concentration and area were adjusted to $2 \times 10^5$ cells/mL and 3.5 cm$^2$.

At 7, 10 and 14 days from the start of culture, the cells were counted and diluted to $2-5 \times 10^5$ cells/mL with CellGro medium containing 1 vol % autoplasma. 1-10-fold feeder cells were prepared and suspended in CellGro medium (Cellgenix) containing 1 vol % autoplasma, followed by irradiation with 2000 cGy in a gamma-ray irradiator. 500 IU of IL-2 and 10 ng/mL of OKT-3 were added thereto, and the two types of cells were co-cultured.

The cells were re-stimulated with feeder cells, followed by stationary culture. Then, the cells were counted at 2-3 day intervals and subjected to suspension culture until day 21 while they were diluted to $5-10 \times 10^5$ cells/mL with CellGro medium (Cellgenix) containing 500 IU of IL-2 and 1 vol % autoplasma. At 21 days of suspension culture, NK cells were collected.

The collected NK cells were suspended to $1-5 \times 10^7$ cells/mL in Hatmann's solution (Choongwae Pharmaceutical Corp., Korea) containing 1 wt % albumin (Green Cross Corp.) and were stored at 4° C.

The results of re-stimulation with feeder cells are shown in FIG. 1(a). As can be seen therein, when stimulation was applied twice or three times, the proliferation of NK cells can be greatly increased compared to when stimulation was applied once. The existing production method showed an NK cell proliferation of about 161 folds, whereas the proliferation of NK cells was increased by 425 folds upon stimulation twice with feeder cells, and 1,320 folds upon stimulation three times with feeder cells. As shown in FIG. 1(b), when stimulation with feeder cells was additionally performed at 7 days or 10 days, the proliferation of NK cells was higher than that in the case in which NK cells were cultured without additional stimulation. Thus, it was found that the novel culture method which comprises applying additional stimulation with feeder cells and adjusting the amount of medium while maintaining the cell number at a constant level is very effective for the proliferation of NK cells compared to the method which comprises applying stimulation once at an initial stage and proliferating NK cells on the basis of the amount of medium rather than the number of cells.

(2) In Vitro Cell Viability of NK Cells

In order to comparatively evaluate in vitro cell viability, a NucleoCounter (Chemometec) system, a cell counter method that uses a PI staining solution capable of binding to intracellular nuclei, was used.

Cells cultured without re-stimulation and cells cultured with re-stimulation at 7 days and 10 days were 10-fold diluted with PBS, and then total cell count and dead cell count were measured using the NucleoCounter system. 100 μL of the 10-fold-diluted cells were mixed with 100 μL of the lysis buffer Solution A-100 (Chemometec), and 100 μL of the stabilizing buffer Solution B (Chemometec) was added thereto, after which total cell count was measured using the piston of NucleoCasette. Dead cell count was measured the piston of NucleoCasette without treating the 10-fold-diluted cells.

The number of viable cells was determined by subtracting the measured dead cell count from the measured total cell count, and then cell viability was calculated using the following equation.

$$\text{Cell viability (\%)} = (\text{viable cell count}/\text{total cell count}) \times 100$$

Figure 2:
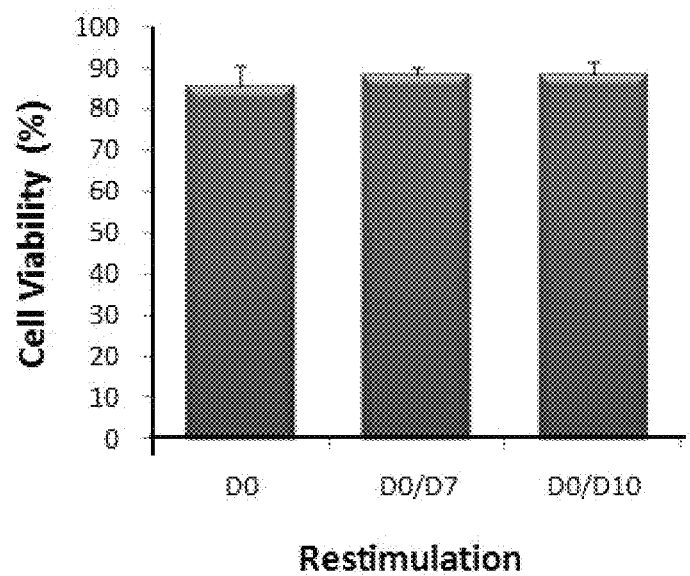
FIG. 2 shows a change in the cell viability of NK cells cultured by re-stimulation with feeder cells, wherein D0: application of stimulation once at day 0; D0/D7: application of stimulation twice at days 0 and 7; and D0/D10: application of stimulation twice at days 0 and 10.

As a result, as can be seen in FIG. 2, NK cells cultured for 21 days with re-stimulation by feeder cells showed a high proliferation rate compared to NK cells cultured without re-stimulation while these NK cells showed a high cell viability of about 90%.

(3) In Vitro Cytotoxicity

A target cancer cell line (K562, etc.) was recovered, and $3 \times 10^6$ cells were placed in a 15 mL tube and centrifuged. The cell pellets were suspended in 600 μL of RPMI medium and 400 μL of the suspension was transferred into a 15 mL fresh tube, and Calcein-AM (Molecular probe, C34852) was added thereto at a concentration of 50 nM. Then, the cell suspension was stained in an incubator at 37° C. for 20 minutes while light was blocked with a silver foil. Meanwhile, 200 μL of the remaining cell suspension was added to 800 μL of RPMI medium at a concentration of $1 \times 10^6$ cells/mL. The cancer cell line subjected to Calcein-AM staining was washed with 15 mL of RPMI medium and centrifuged, and the pellets were suspended in 2 mL of RPMI medium at a concentration of $1 \times 10^6$ cells/mL.

3×10⁶ NK cells were placed in a 15 mL tube and centrifuged, and the pellets were suspended in RPMI medium at a desired ratio relative to the target cancer cell line. 100 μL of a mixture of the prepared target cancer cell line and the NK cell line was dispensed into each well of a round-bottom 96-well plate. Each well was prepared in duplicate. The plate was incubator at 37° C. for 2 hours in a light-shielded state, and then centrifuged at 2000 rpm for 3 minutes. The supernatant was removed, and 100 μL of FACS buffer (2.5 wt % FBS in PBS) was added to each well of the plate to suspend the cells, after which the plate was transferred into a FACS containing 5 μL of 7-AAD (BD, 559925). After incubation at room temperature for 20 minutes, the cancer cytotoxicity of NK cells was analyzed as follows:

Cytotoxicity=$A$ value–$B$ value

'A value' means ratio of target cancer cells killed when NK cells were incubated with target cancer cells (average value of dead target cancer cells stained with both Calcein-AM and 7-AAD—control stained with only Calcein-AM)

'B value' means ratio of basically dead target cancer cells (dead target cancer cells stained with both Calcein-AM and 7-AAD—control stained with only Calcein-AM)

Figure 3:
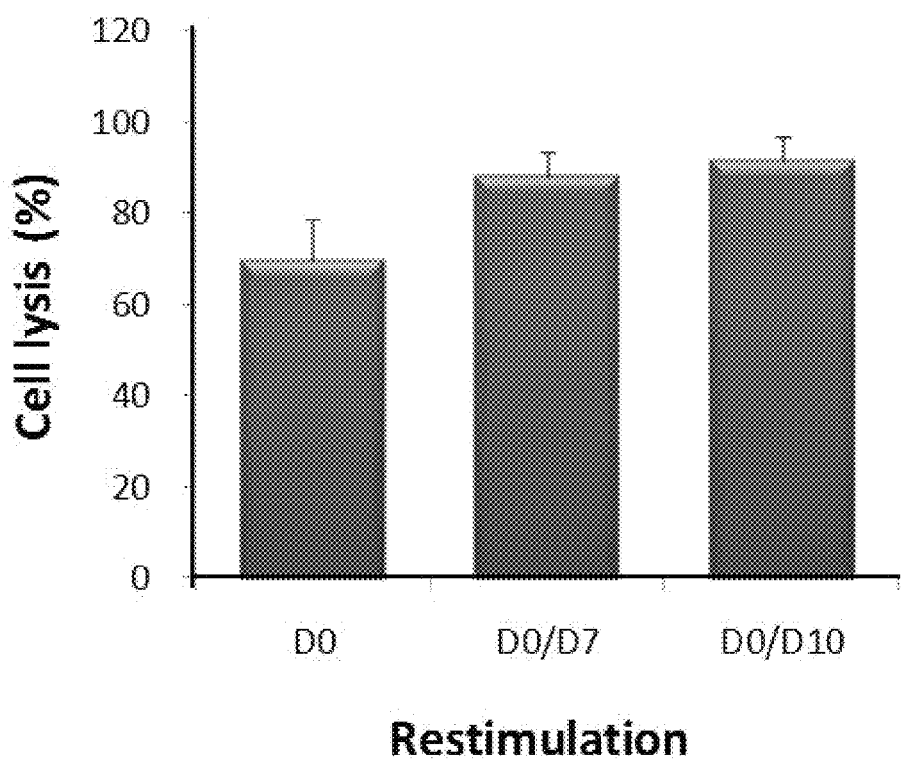
FIG. 3 shows a change in the cytotoxicity of NK cells cultured by re-stimulation with feeder cells, wherein D0: application of stimulation once at day 0; D0/D7: application of stimulation twice at days 0 and 7; and D0/D10: application of stimulation twice at days 0 and 10.

As a result, as can be seen in FIG. 3, while NK cells cultured for 21 days with re-stimulation by feeder cells showed high proliferation rate compared to NK cells cultured without re-stimulation, they showed a high cytotoxicity of about 90% at E:T ratio=3:1.

(4) In Vitro Cell Phenotype Analysis

NK cells were collected before and after culture in Example 1(1) and centrifuged at 1200 rpm for 5 minutes, and the medium was removed by suction. The cells were diluted with 1 mL of FACS buffer (2.5% FBS containing PBS), counted and diluted with FACS buffer at a concentration of 5×10⁶ cells/mL. 100 μL of the diluted cell solution was added to each of 5 mL FACS tubes (Falcon, 352052), and the antibodies shown in Table 1 below were added thereto.

TABLE 1

| | Antibodies added to each tube |
|---|---|
| Tube 1 | anti-human CD3-FITC (BD Pharmingen, 555332), anti-humanCD16-PE (BD Pharmingen, 555407), anti-human CD56-PE-Cy5 (BD Pharmingen, 555517) |
| Tube 2 | anti-human CD14-FITC (BD Pharmingen, 555397), anti-human CD19-PE (BD Pharmingen, 555413), anti-human CD3-PE-Cy5 (BD Pharmingen, 555341) |
| Tube 3 | anti-human CD3-FITC, anti-human NKG2A-PE (R&D system, FAB1059P), anti-human CD56-PE-Cy5 |
| Tube 4 | anti-human CD3-FITC, anti-human NKG2C-PE (R&D system, FAB138P), anti-humanCD56-PE-Cy5 |
| Tube 5 | anti-human CD3-FITC, anti-human NKG2D-PE (R&D system, FAB139P), anti-human CD56-PE-Cy5 |
| Tube 6 | anti-human CD3-FITC, anti-human HKp30-PE (BD Pharmingen, 558407), anti-human CD56-PE-Cy5 |
| Tube 7 | anti-human CD3-FITC, anti-human HKp44-PE (BD Pharmingen, 558563), anti-humanCD56-PE-Cy5 |
| Tube 8 | anti-human CD3-FITC, anti-human NKp46-PE (BD Pharmingen, 557991), anti-human CD56-PE-Cy5 |
| Tube 9 | anti-human CD3-FITC, anti-human CD158a-PE (Beckman Coulter, A09778), anti-humanCD56-PE-Cy5 |
| Tube 10 | anti-human CD3-FITC, anti-human CD158b-PE (Beckman Coulter, IM2278U), anti-human CD56-PE-Cy5 |
| Tube 11 | anti-human CD3-FITC, anti-human CD158e-PE (Beckman Coulter, IM3292), anti-human CD56-PE-Cy5 |
| Tube 12 | anti-human CD3-FITC, anti-human CD25-PE (BD Pharmingen, 555432), anti-human CD56-PE-Cy5 |
| Tube 13 | anti-human CD3-FITC, anti-human CD62L-PE (eBioscience, 12-0629-42), anti-human CD56-PE-Cy5 |

TABLE 1-continued

| | Antibodies added to each tube |
|---|---|
| Tube 14 | anti-human CD57-FITC (BD Pharmingen, 555619), anti-human CD3-PE (BD Pharmingen, 555333), anti-human CD56-PE-Cy5 |
| Tube 15 | FITC mice IgG1 k isotype control (BD Pharmingen, 555748), anti-human CD3-PE (BD Pharmingen, 555333), anti-human CD56-PECy5 |
| Tube 16 | anti-human CD3-FITC, PE mice IgG1 k isotype control (BDPharmingen, 555749), anti-human CD56-PE-Cy5 |

Control tubes were prepared as shown in Table 2 below.

TABLE 2

| | Control Tube |
|---|---|
| Tube C1 | FITC mice IgG1 k isotype control PE mouse IgG1 k isotype control, PE-Cy5 mice IgG1 k isotype control (BD Pharmingen, 555750) |
| Tube C2 | anti-human CD16-FITC (BD Pharmingen, 555406), PE mice IgG1 k isotype control, PE-Cy5 mice IgG1 k isotype control |
| Tube C3 | FITC mice IgG1 k isotype control, anti-human CD56-PE (BD Pharmingen, 555516), PE-Cy5 mice IgG1 k isotype control |
| Tube C4 | FITC mice IgG1 k isotype control, PE mice IgG1 k isotype control, anti-human CD56-PE-Cy5 |

The tubes shown in Tables 1 and 2 were allowed to stand at refrigeration temperature to stain the cells. The stained cells were added to 2 mL of FACS buffer and centrifuged at 1500 rpm for 5 minutes. The supernatant was removed, and the pellets were added to 2 mL of FACS buffer and centrifuged at 1500 rpm for 5 minutes. Next, the supernatant was removed, and the pellets were suspended in 300 μL of FACS buffer, after which the cell phenotype was analyzed using FACSCalibur (Becton Dickinson).

Figure 4:
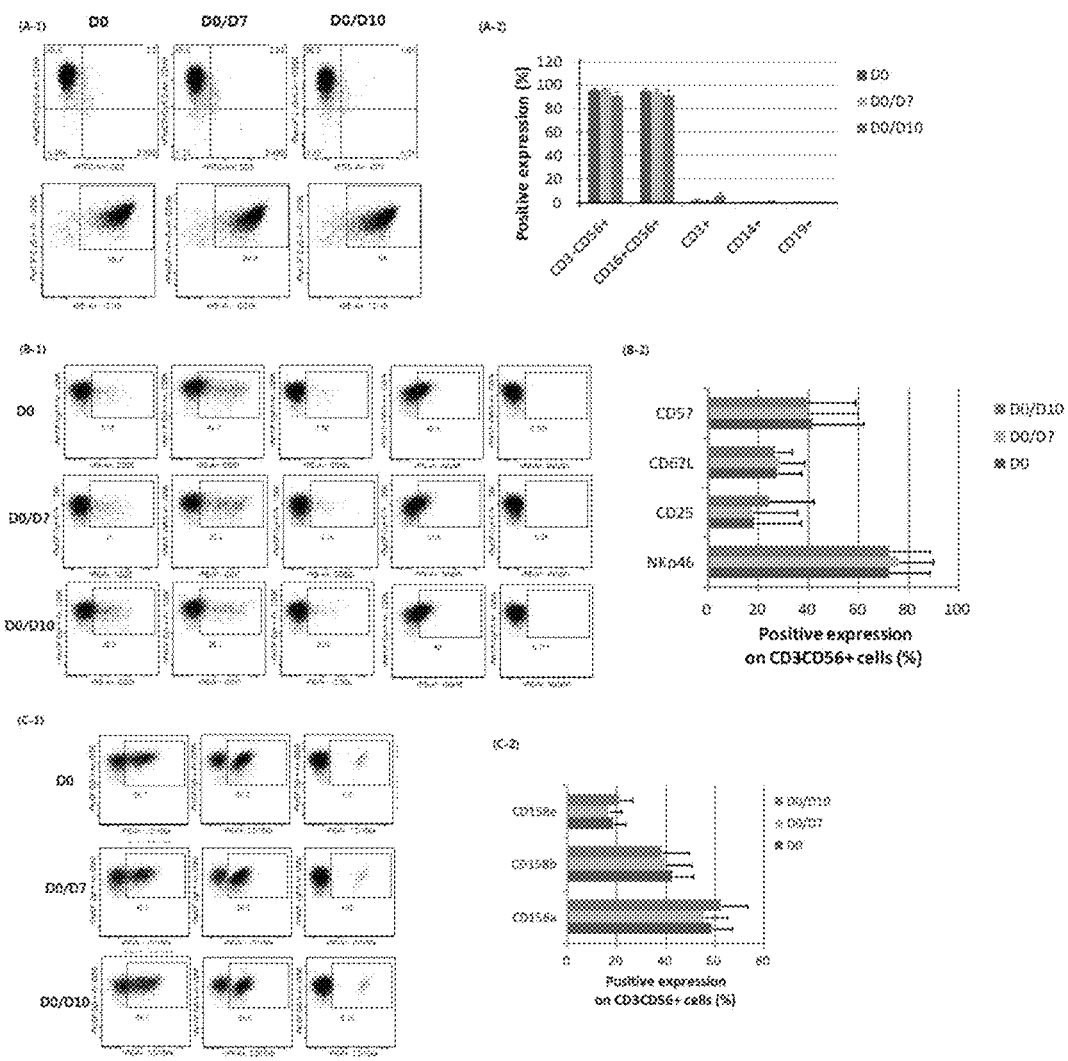
FIG. 4 shows analysis results for the phenotype of NK cells cultured by restimulation with feeder cells, wherein (a1 & a2): identity and purity of NK cells; (b1 & b2): activating receptors of NK cells; and (c1 & c2): inhibitory receptors of NK cells.

As a result, as can be seen in FIG. 4, the phenotype corresponding to identification and purity and the phenotype related to the activation and inhibition of NK cells did not significantly differ between the case in which additional stimulation by feeder cells was performed and in the case in which no additional stimulation was performed.

Thus, while NK cells produced by the improved culture method comprising re-stimulation with feeder cells show high proliferation rate compared to NK cells cultured by an existing method, the cell viability, cytotoxicity and cell phenotype thereof do not significantly differ from those of the NK cells cultured by the existing method.

Example 2: In Vitro Stability (Stability in Use) Resulting from Addition of Albumin In order to evaluate the stability of cultured cells as a function of the concentration of albumin in Hatmann's solution (2 wt %, 1 wt %, and 0.5 wt %), the cells cultured in Example 1(1) were stored at 4° C. for 72 hours while the in vitro cytotoxicity and in vitro cell viability thereof were evaluated at 24-hour intervals.

The finally cultured NK cells were centrifuged, and the supernatant was removed. The cell pellets were diluted in Hatmann's solution or a Hatmann's solution containing human serum albumin at concentrations of 2 wt %, 1 wt % and 0.5 wt %, thereby making cell dilutions. Herein, the concentration of the final cell dilution was adjusted to 1.1×10⁷ cell/mL by controlling the amount of Hatmann's solution or the human serum albumin-containing Hatmann's solution, and then the cell dispersions were placed in cell culture bags and stored at 4° C. After 24, 48 and 72 hours, the cells were taken out and the in vitro cytotoxicity (see Example 1(3)) and in vitro cell viability (see Example 1(2)) thereof were evaluated.

Figure 5:
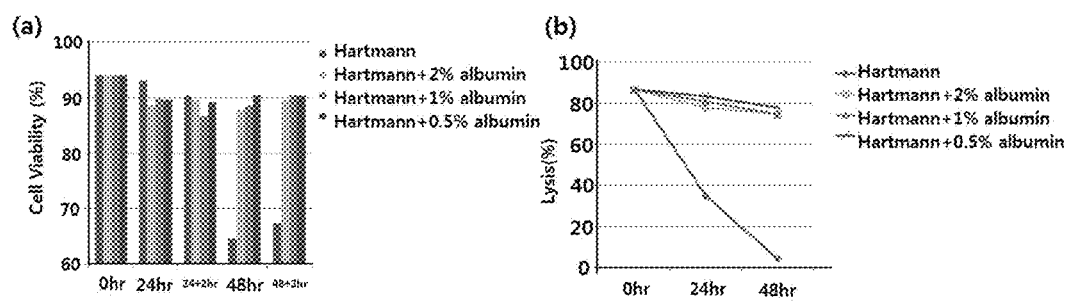
FIG. 5 shows the changes in cell viability and cytotoxicity according to the concentration of albumin in a composition containing NK cells, wherein (a) change in the viability of NK cells; and (b) change in the cytotoxicity of NK cells.

As a result, as can be seen in FIG. 5(a), when the cells were cold-stored in Hatmann's solution up to 48 hours, the cell viability decreased to 65%. However, when human albumin was added at a concentration of 1 wt %, a cell viability of about 90% was still maintained even when the cells were cold-stored up to 48 hours or were stored at room temperature for 2 hours in view of time in use.

FIG. 5(b) shows cytotoxicity as a function of storage time. As can be seen therein, when the cells were stored in Hatmann's solution, the cytotoxicity started to decrease rapidly from 24 hours and decreased to less than 10% at E:T ratio=3:1 at 48 hours. However, when 1 wt % of human albumin was added, the NK cells showed a high cytotoxicity of 70% or more even after cold storage for 48 hours.

Figure 6:
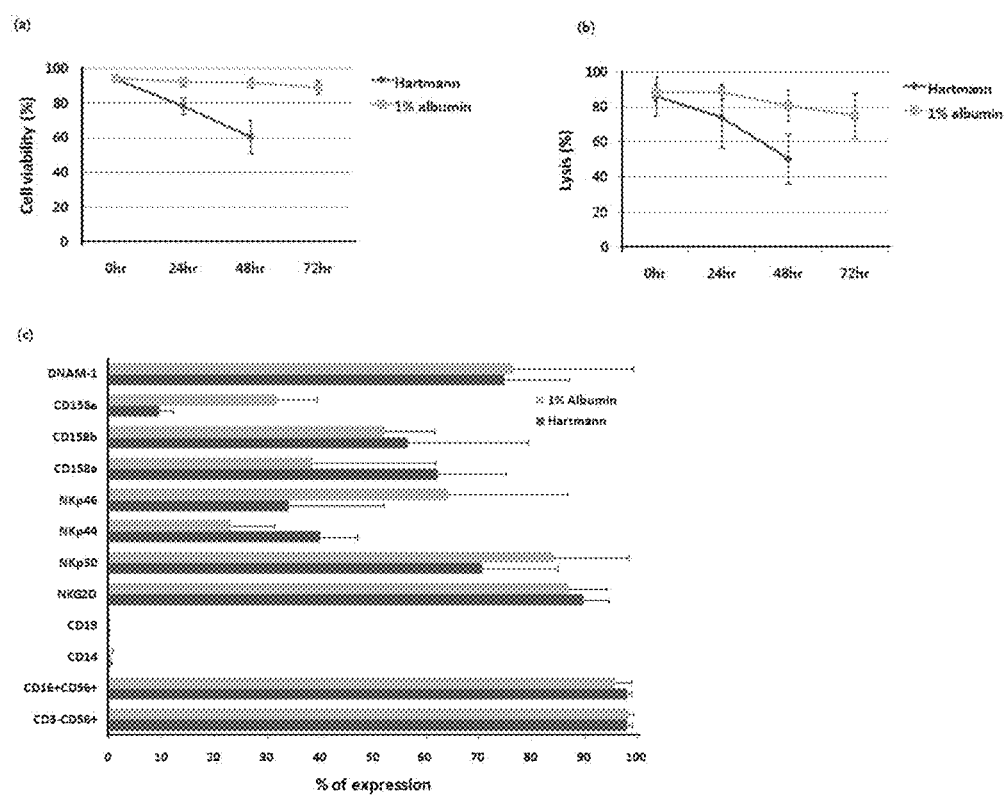
FIG. 6 shows the changes in cell viability, cytotoxicity and phenotype of NK cells in a composition, which result from the addition of albumin, wherein (a) change in the viability of NK cells; (b) change in the cytotoxicity of NK cells; and (c) change in the phenotype of NK cells.

FIG. 6 shows a comparison of cumulative data between Hatmann's solution and 1 wt % human albumin-Hatmann's solution. As shown in FIG. 6(a), when 1 wt % albumin was added, a high cell viability of 80% or more was maintained up to 72 hours. However, in Hatmann's solution, the cell viability decreased rapidly to 60% at 48 hours. FIG. 6(b) shows a comparison of cytotoxicity at E:T ratio=3:1. As can be seen therein, when 1 wt % albumin was added, a cytotoxicity of 70% or more was maintained up to 72 hours, whereas in Hatmann's solution, the cytotoxicity decreased to 50% at 48 hours. FIG. 6(c) shows the results of observing the difference in the phenotype of NK cells between the above two conditions. As can be seen therein, NKp46 which is connected directly with cytotoxicity was highly expressed in the condition in which 1 wt % albumin was added, and other phenotypes did not significantly differ between the two conditions.

Thus, it can be seen that addition of 1 wt % human albumin to the final NK cell therapeutic agent greatly contributes to ensuring the stability of the NK cells by maintaining the cell viability and cytotoxicity of the NK cells with the passage of time.

Example 3: NK Cell Freezing and Thawing Tests: Cell Number, Yield, Phenotype, Viability and Cytotoxicity The freezing stability of NK cells cultured in Example 1(1) was examined.

To freeze the cultured NK cells, the cell number was adjusted to $2-8\times10^7$ cells/mL, and the cells to be frozen were transferred into a separate tube and then centrifuged at 1200 rpm for 10 minutes at 4° C. Freezing in a freezing bag (MEDIRUTION, Korea) was based on 20 mL. The centrifuged cells were suspended well with 14 mL of human serum AB. 4 mL Dextran 40 and 2 mL DMSO were mixed with each other and cooled, and the mixed solution was dropped into the prepared cell suspension with stirring. The cells were injected into the freezing bag, and bubbles were removed from the bag. The freezing bag was freezed with controlled-rate freezer (CryoMed freezer, Thermo Scientific) and stored in a liquid nitrogen tank.

For thawing, the freezing bag was taken out from the nitrogen tank, placed in a zipper bag and thawed rapidly in an incubator at 37° C. After the cells have completely thawed, the cells were transferred into the corresponding tube and suspended slowly with a 10-fold amount of PBS solution containing 1 wt % FBS. The cell suspension was mixed well and centrifuged (1,200 rpm, 10 min, 4° C.). After centrifugation, the cells were suspended with 1 wt % FBS-containing PBS at a concentration of $10^7$ cells/mL. After 10-fold dilution, the cell number and viability were measured. Based on the measured cell number, cytotoxicity against the K562 cell line was evaluated at E:T ratio=3:1. The cell phenotype was measured for CD16, NKG2A, NKG2C, NKG2D, NKp30, NKp44, NKp46, CD25, CD62L, CD57 and the like. Finally, the changes in cell yield, viability, cytotoxicity and cell phenotype between before and after freezing were evaluated.

Figure 7:
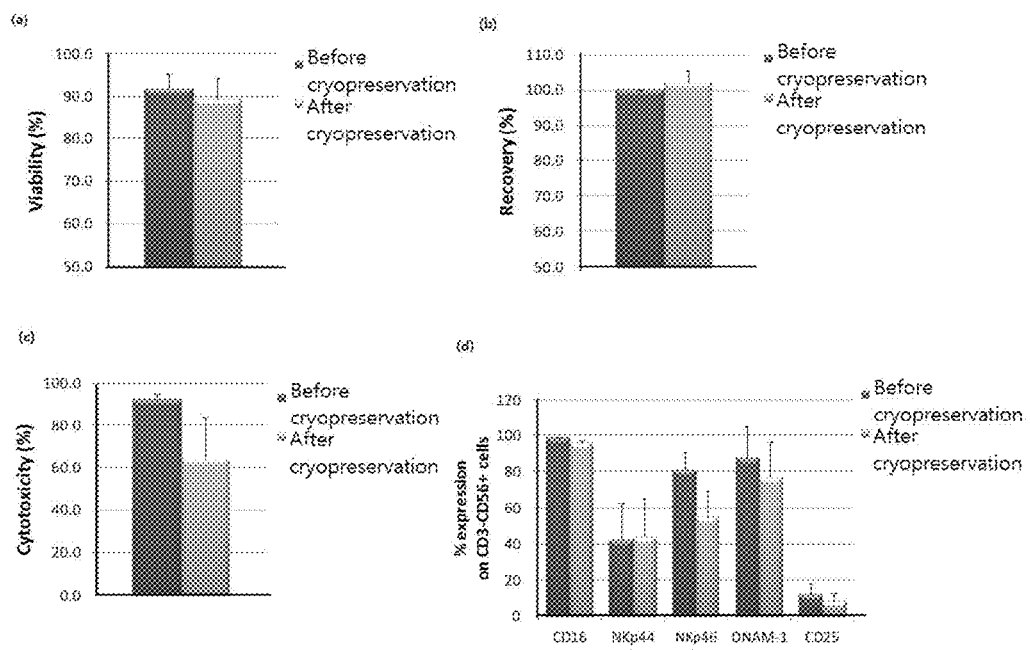
FIG. 7 shows the change in NK cells resulting from freezing, wherein (a) cell viability after freezing/thawing; (b) recovery after freezing/thawing; (c) cytotoxicity after freezing/thawing; and (d): expression level of cell phenotypes on CD56+ cells after freezing/thawing.

As a result, when the cultured NK cells were thawed after freezing, they maintained high cell viability (see FIG. 7(a)) and recovery (see FIG. 7(b)), had high cytotoxicity against the K562 cancer cell line without requiring special activity induction (see FIG. 7(c)), and also maintained cell phenotypes (see FIG. 7(d)).

Example 4: Evaluation of Anticancer Effect of Natural Killer Cells in Lymphoma Animal Model (1) Construction of Lymphoma Animal Model
1) Culture of Raji and SU-DHL-4 Cell Lines The Raji (human B cell lymphoma cell line, ATCC, CCL-86) and SU-DHL-4 (human B cell lymphoma cell line, DSMZ, ACC 495) cell lines were cultured in a 5% CO2 incubator at 37° C. using RIMI medium (2 mM L-glutamine, 1 mM sodium pyruvate, 10 wt % FBS, 0.055 mM 2-mercaptoethanol, 100 U/ml penicillin, 100 ug/ml streptomycin).

2) Construction of Animal Model 6-8-week-old female C.B-17 mice were acclimated for 7 days, and then each of the Raji and SU-DHL-4 cell lines was injected into the tail vein of the mice by a 1 mL syringe at a concentration of $1\times10^5$ cells/100 µL.

(2) Administration of Natural Killer Cells and Evaluation of Anticancer Effect
1) Administration of Natural Killer Cells After xenograft of cancers, the mice were grouped randomly and marked. 400 µL of PBS was injected into the tail vein of the control group. In the test group, natural killer cells were administered 5 times into the tail vein of the mice at a concentration of $1\times10^7$ cells/400 µL at 2-3-day intervals from 0 day.

2) Evaluation of Anticancer Effect

After the experiment, the general conditions, mobility and hind extremity paralysis of the mice were examined daily. When Raji and SU-DHL-4 are administered intravenously into mice which are well known lymphoma models, tumors are created around the spinal cord, and thus the mice show hind extremity paralysis symptoms and lead to death after 2-3 days. Thus, the development of hind extremity paralysis was evaluated together with survival rate and used as an index of anticancer effect.

Figure 8:
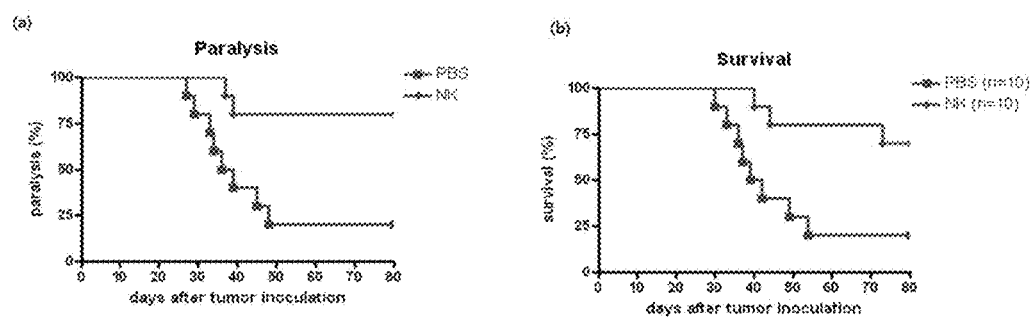
FIG. 8 shows the anticancer effect of NK cells in a lymphoma animal model, wherein (a) the effect on the alleviation of hind leg paralysis in test model; and (b) the effect on improvement in the survival of test model.

As a result, in the control group administered with PBS, the median values of hind extremity paralysis (see FIG. 8(a)) and survival rate (see FIG. 8(b)) were 37 days and 39 days, whereas in the group administered with the NK cells, hind extremity paralysis was clearly alleviated such that the median value was not determined, and the survival rate was greatly increased.

Example 5: Evaluation of Anticancer Effect of Natural Killer Cells in Brain Cancer (Glioblastoma) Animal Model (1) Construction of Brain Cancer Animal Model U-87 MG (human glioblastoma cell line, ATCC HTB-14) was injected into the cerebrum of 6-week-old BALB/C-nu/nu mice using a multi-syringe injector with seven flames at a concentration of $2\times10^5$ cells/5 µL. The cells were injected using a Hamilton syringe, and the needle of the syringe was removed for 5 minutes after 5-minute rest. Then, disinfection and suture were performed. The condition and weight of the mice were observed during the test period. The mice were sacrificed according to the test schedule, and the tissue was analyzed.

(2) Administration of Natural Killer Cells

In order to examine the anticancer effect of NK cells in the brain cancer animal model, NK cells were injected three times at one-week intervals from 1 week after administration of U-87MG. The NK cells were injected intracranially and intravenously. In the case of intracranial injection, $1 \times 10^3$, $1 \times 10^4$ and $1 \times 10^5$ NK cells were administered, and in the case of intravenous injection, $1 \times 10^5$, $1 \times 10^6$ and $1 \times 10^7$ NK cells were administered. 4 weeks after administration of U-87MG, the mice were sacrificed and the anticancer effect of the NK cells was evaluated.

In order to examine anticancer effects resulting from the combined administration of NK cells and an anticancer agent and the time point of administration, $1 \times 10^7$ NK cells were intravenously injected at various points of time as shown in Table 3 below. Temozolomide (TMZ) as an anticancer agent was intraperitoneally injected at a dose of 2.5 mg/kg once a day for 5 consecutive days from 3 weeks after administration of U-87MG. At 4 weeks after administration of U-87MG, the mice were sacrificed and the tumor volume was measured.

TABLE 3

Combination of NK and anticancer agent and administration method in each group

| Group | | Description |
|---|---|---|
| 1 | Control | Transplanted only with cancers; no additional treatment |
| 2 | NK cell | Administration of NK cells three times at one-week intervals from 1 week after administration of cancers |
| 3 | TMZ | Administration of TMZ once a day for 5 consecutive days from 3 weeks after administration of cancers |
| 4 | NK cell/TMZ | Administration of NK cells three times at one-week intervals from 1 week after administration of cancers Administration of TMZ once a day for 5 consecutive days from 3 weeks after administration of cancers |
| 5 | NK cell (3 wk) | Administration of NK cells three times at 2-day intervals from 3 weeks after administration of cancers |
| 6 | NK cell (3 wk)/TMZ | Administration of NK cells three times at 2-day intervals from 3 weeks after administration of cancers Administration of TMZ once a day for 5 consecutive days from 3 weeks after administration of cancers |
| 7 | NK cell (1 wk) | Administration of NK cells three times within 1 weeks after administration of cancers |

(3) Evaluation of Anticancer Effect

To measure the volume of tumors, hematoxylin-eosin staining was used. The brain was extracted from the mice and sectioned at 2 mm intervals. The sections were fixed in 10% buffered formalin solution at 4° C. for 24 hours and embedded in paraffin block. The paraffin-embedded tissue was sectioned to 4 μm, mounted onto coated slide glass and dried overnight. The tissue was de-paraffinized with xylene and rehydrated through a graded alcohol series (100 vol %, 95 vol % and 80 vol % ethanol/distilled water. Then, the tissue was subjected to Gill's hematoxylin-eosin staining, and the degree of staining was examined, followed by dehydration and mounting. The length and width of the tumor in the stained tissue were measured and the tumor volume was calculated using the following equation:

$$\text{Tumor volume (mm}^3\text{)} = \text{tumor length (mm)} \times \text{tumor width (mm)}^2 \times 0.5$$

Figure 9:
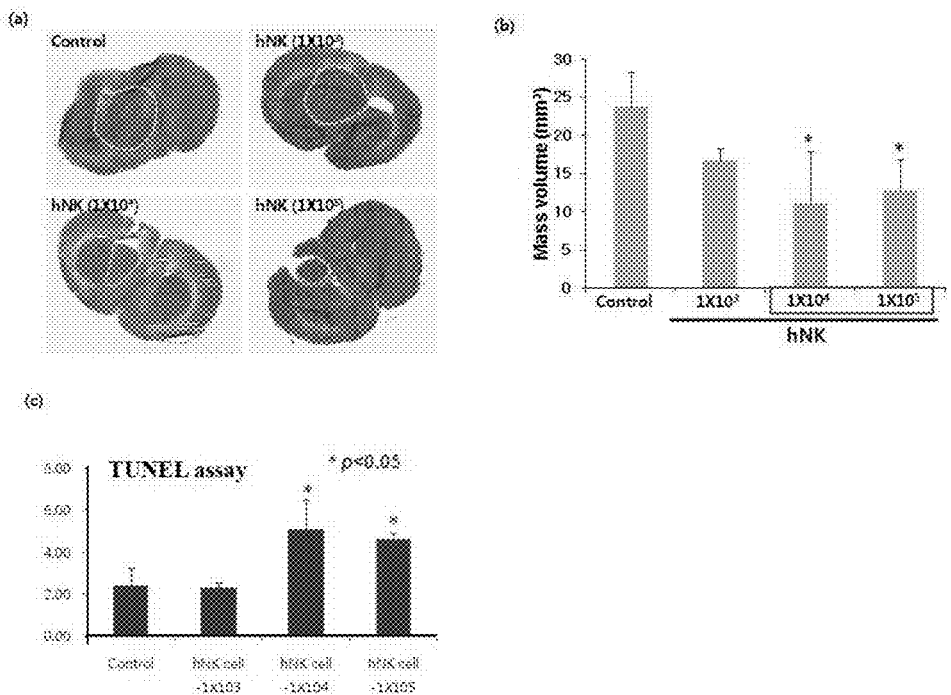
FIG. 9 shows the anticancer effect of NK cells in a brain cancer (glioblastoma) animal model upon intracranial administration, wherein (a) the results of observing the tumor volume by histological examination; (b) the results of TUNEL analysis according to the cell number; and (c) the change in tumor volume according to the number of NK cells.
Figure 10:
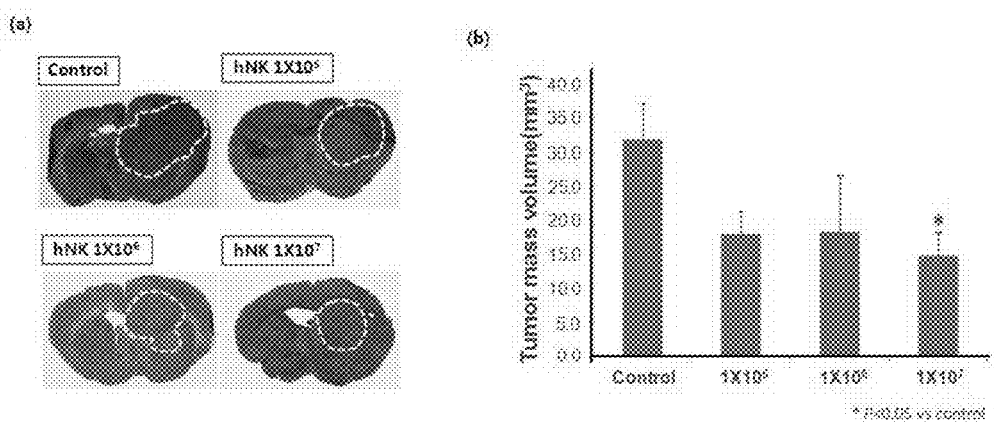
FIG. 10 shows the anticancer effect of NK cells in a brain cancer animal model upon intravenous administration, wherein (a): the results of observing tumor volume by histological examination; and (b) the change in tumor volume according to the number of NK cells.
Figure 11:
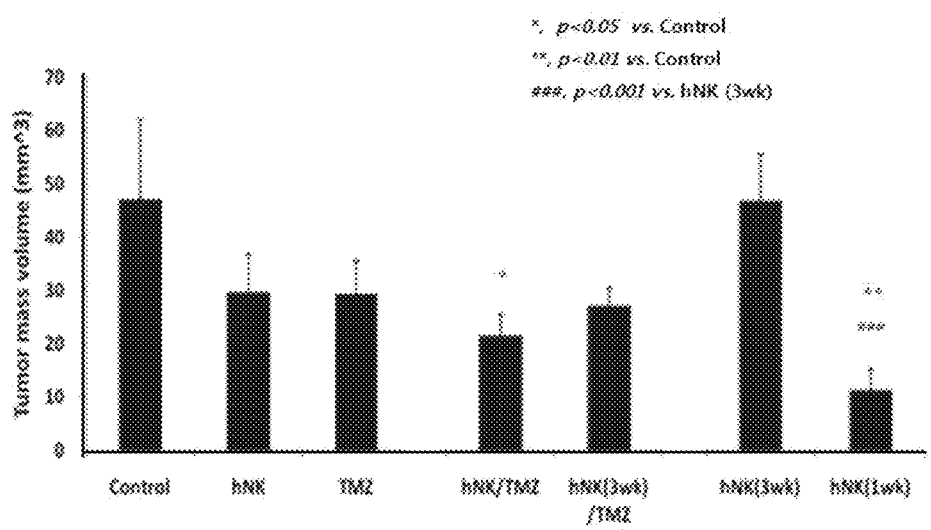
FIG. 11 shows the anticancer effect of NK cells in a brain cancer animal model when administered in combination with an anticancer agent.

It could be seen that, when $1 \times 10^4$ and $1 \times 10^5$ NK cells were administered intraperitoneally (see FIG. 9) and $1 \times 10^6$ and $1 \times 10^7$ NK cells were administered intracranially (see FIG. 10), the tumor volume was reduced compared to the control. When effects resulting from the combined administration of NK cells and the anticancer agent and the time point of administration were observed (see FIG. 11), it could be seen that the tumor volume was smaller when TMZ and NK cells were administered in combination than when they were administered alone. In addition, when NK cells were injected three times within 1 week after administration of cancer, the tumor volume was most significantly reduced, suggesting that the best effect was shown.

To analyze the degree of cell death, a TUNEL (terminal deoxynucleotidyl mediated deoxyuridine triphosphate nick-end labeling) assay) was performed. Specifically, paraffin-embedded tissue (4 mm) was mounted onto coated slide glass and dried overnight. The tissue was de-paraffinized with xylene and rehydrated through a graded alcohol series (100 vol %, 95 vol % and 80 vol % ethanol/distilled water, followed by washing with PBS (pH 7.5). The degree of cell death in the tissue was examined using a TUNEL kit (Invitrogen). The stained slide was counterstained with Gill's hematoxylin for 1 minute and mounted. The stained slide was photographed with a microscope at 400× magnification with respect to the cancer edge to obtain 10 photographs, and the cells were counted with respect to the cells showing a positive response, and the measurements were averaged.

As a result, it can be seen that, when $1 \times 10^4$ and $1 \times 10^5$ NK cells were administered intracranially, the number of dead cells was large, suggesting that the administration of NK cells was effective (see FIG. 9c).

Example 6: Evaluation of Anticancer Effect of NK Cells in Ovarian Cancer Animal Model (1) Construction of Ovarian Cancer Animal Model
1) Construction of OVCAR-3-Luc Cell Line Luciferase gene was cloned into a pGL3 vector and transiently transfected into an OVCAR-3 cell line. Cell lines showing the expression of luciferase were primarily selected using luciferin, and cell lines having the phenotypes and NK cytotoxicities similar to those of OVCAR-3 were secondarily selected.

2) Culture of OVCAR-3-Luc Cell Line

The OVCAR-3-Luc (human ovarian cancer cell line, KTCC (Korean Cell Line Bank) 30162) cell line was incubated at 37° C. in a 5% $CO_2$ incubator using RIMI medium (2 mM L-glutamine, 1 mM sodium pyruvate, 10% FBS, 0.055 mM 2-mercaptoethanol, 100 U/ml penicillin, 100 μg/ml streptomycin, 100 μg/mL G418).

3) Construction of Animal Model 6-8-week-old female C.B-17 SCID mice were acclimated for 7 days, and the OVCAR-3-Luc cell line was injected intraperitoneally into the mice at a concentration of $5 \times 10^6$ cells/100 μL.

(2) Administration of NK Cells and Evaluation of Anti-cancer Effect

1) Administration of NK Cells

After xenograft of cancers, the mice were grouped randomly and marked. The control group was injected intraperitoneally with 200 µL of Hatmann's solution (Choongwae Pharmaceutical Corp., Korea). The NK cell-treated group was intraperitoneally injected five times with $1\times10^7$ NK cells/200 µL at 2-3-day intervals from 1 week after xenograft of cancers.

2) Evaluation of Anticancer Effect

After xenograft of OVCAR-3-Luc, the general conditions and mobility of the mice were observed daily. Luciferin was administered intraperitoneally to the mice, and luciferase images were photographed using an IVIS imaging system (Xenogen) at 7-day intervals. 8 weeks after xenograft of the cancer, the abdomens of the mice of all the groups were open, and the volumes of tumors were measured.

Figure 12:
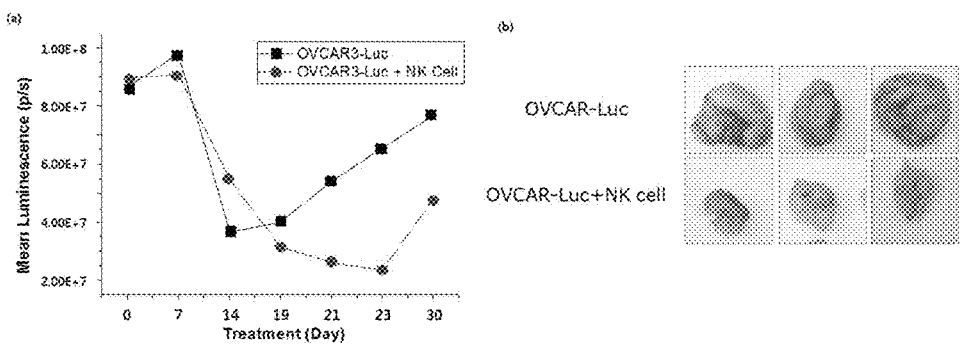
FIG. 12 shows the anticancer effect of NK cells in an ovarian cancer animal model, wherein (a) the change of tumor size as a function of the administration period of NK cells (in vivo images); and (b) the results of observing the change in tumor size resulting from NK cell administration.

Immediately after xenograft of the cancer cells, the cancer cells spread throughout the abdominal cavity, and the luciferase image appeared to be large. However, after 7 days, the cancer cells were engrafted, and thus the luciferase level decreased. After 7 days, in the group administered with NK cells, the luciferase level decreased continuously up to 23 days, whereas in the negative control group, the luciferase level increased. (see FIG. 12 (a)).

At 8 weeks, the mice were sacrificed, the tumor was extracted, and the volume and weight of the tumor were measured (see FIG. 12(b)). It was observed that the weight of the tumor in the NK cell-administered group decreased by 54.91% compared to that in the negative control group. In other words, the tumor volume in the NK cell-administered group significantly decreased compared to that in the negative control group. This suggests that when NK cells are administered intraperitoneally to a model having ovarian cancer metastasized to the abdominal cavity, they inhibit the growth of the tumor.

Example 7: Evaluation of Anticancer Effect of NK Cells in a Human Liver Cancer Animal Model (1) Construction of a Liver Cancer Animal Model To evaluate the anticancer effect of NK cells on liver cancer, a human tumor xenograft mouse model was constructed and the NK cells were administered intravenously. For this, $6\times10^6$ cells of SNU-354 cells, a human liver cancer cell line, were implanted subcutaneously to the side of a nude mouse.

(2) Administration of NK Cells and Evaluation of Anticancer Effect

1) Administration of NK Cells

Two hours after xenografting of SNU-354 cells, $1\times10^6$ cells or $1\times10^7$ cells of NK cells were administered in 200 µL via the tail vein of the mouse. After the first administration, the same dose of NK cells was injected 3 times more at an interval of a week.

TABLE 4

Methods of administration of NK cells according to the group

| group | administration route | dose | Number of mouse | Remarks |
| --- | --- | --- | --- | --- |
| 1 | i.v. | Vehicle (weekly) | 10 | control |
| 2 | i.v. | NK cells ($1 \times 10^6$ cells/mouse, weekly) | 10 | low dose group |
| 3 | i.v. | NK cells ($1 \times 10^7$ cells/mouse, weekly) | 10 | high dose group |

2) Evaluation of Anticancer Effect

To evaluate the toxicity of NK cells during the experiment, the general conditions were observed daily and the animal weight and tumor volume were measured 11 times (day 0, 7, 9, 12, 14, 16, 19, 21, 23, 26, and 28) until the end of the experiments. After 28 days, the animals were sacrificed and the weights of the extracted tumors were measured.

Figure 13:
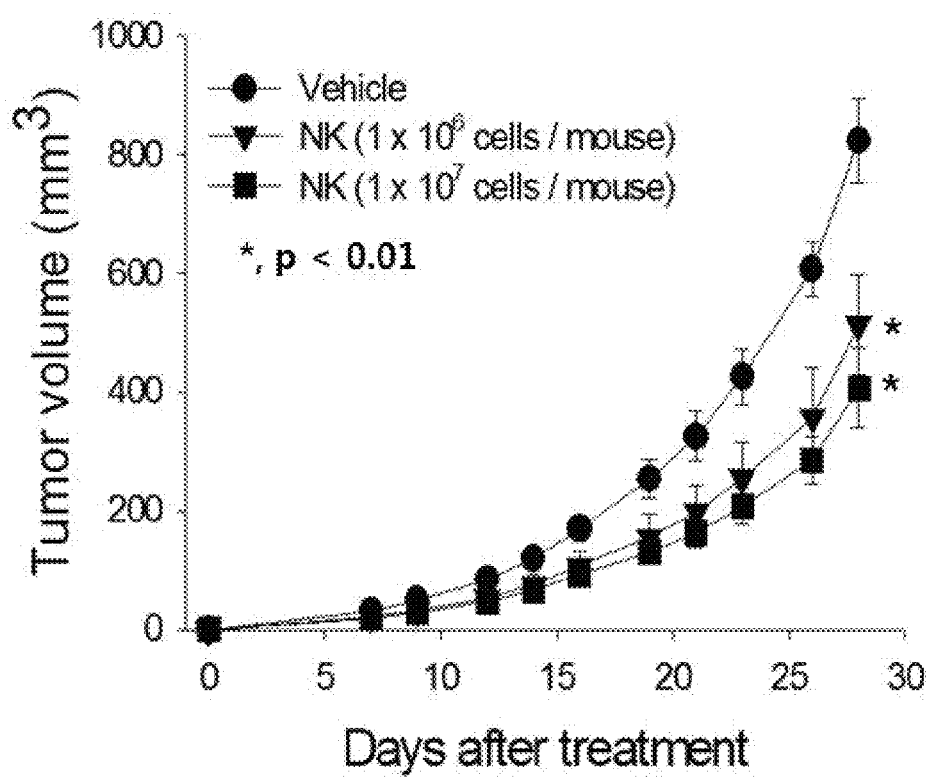
FIG. 13 shows the anticancer effect of NK cells in a liver cancer animal model.

It was observed that the tumor volume of the NK cell-administered group decreased by 37.7% ($1\times10^6$ cells/mouse) and 50.6% ($1\times10^7$ cells/mouse), compared with that of the negative control group (FIG. 13).

In addition, the tumor weight of the NK cell-administered group decreased by 36.0% ($1\times10^6$ cells/mouse) and 50.2% ($1\times10^7$ cells/mouse), compared with that of the negative control group (FIG. 13).

Therefore, it can be concluded that NK cells may be used for liver cancer treatment.

Example 8: Evaluation of Anticancer Effect of NK Cells in Neuroblastoma Animal Model (1) Construction of Neuroblastoma Animal Model 1) Culture of NB-1691 Luc Cell Line The NB-1691 luc cell line, prepared by transfection with luciferase gene into NB-1691(human neuroblastoma cell line, from St. Jude Children's Research Hospital), was incubated at 37° C. in a 5% $CO_2$ incubator using RIMI medium (2 mM L-glutamine, 1 mM sodium pyruvate, 10% FBS, 0.055 mM 2-mercaptoethanol, 100 U/ml penicillin, 100 µg/ml streptomycin, 100 µg/mL G418).

3) Construction of Animal Model 7-week-old female C.B-17 SCID mice were acclimated for 7 days, and the NB-1691 luc cell line was injected into the tail vein of mice at a concentration of $5\times10^5$ cells/100 µL.

(2) Administration of NK Cells and Evaluation of Anticancer Effect

1) Administration of NK Cells

After xenograft of cancers, the mice were grouped randomly and marked. The control group was injected 200 µL of Hatmann's solution (Choongwae Pharmaceutical Corp., Korea) into the vein of tail. The NK cell-treated group was injected five times with $1\times10^7$NK cells/200 µL at 2-3-day intervals from 1 week after xenograft of cancers into the vein of tail.

2) Evaluation of Anticancer Effect

After xenograft of NB-1691 luc, the general conditions and mobility of the mice were observed daily. To follow up tumor growth, Luciferin was administered intraperitoneally to the mice and luciferase images were photographed using an IVIS imaging system (Xenogen) at 7-day intervals.

Figure 14:
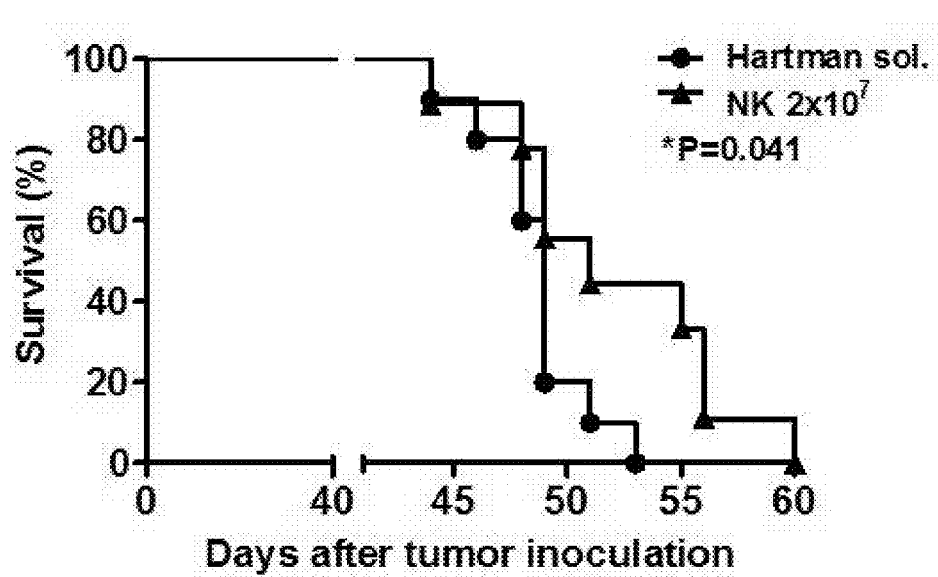
FIG. 14 shows the anticancer effect of NK cells in a neuroblastoma animal model.

During the experiment, investigation was carried out to check death of animal five times per week. As a consequence, days of survival for control group and NK cell administered group were 49 and 51 days, respectively. However, the survival of NK cell administered group increased significantly by log-rank test (FIG. 14).

Example 9: Evaluation of Efficacy of NK Cells on Various Cancer Cell Lines and Virus Infected Cell Lines In Vitro By using NK cells prepared as described in Example 1, cytotoxicity of NK cells were evaluated as described in Example 1(3).

The NK cells' ability of cytokines secretion was measured as follows;

Preparing NK cells ($5\times10^6$ cell/mL) and target cancer cell lines ($5\times10^6$ cell/mL), and adding the prepared NK cells and target cancer cell lines into the round-bottomed 96-well plate. To avoid secretion of cytokines accumulated in the cell of GolgiStop (BD Pharmingen, 554724) was added simultaneously.

Well 1: Suspended NK cells 100 μL, RPMI medium 100 μL, anti-human CD107a-APC (BD Pharmingen, 560664) 1 μL Well 2: Suspended NK cells 100 μL, suspended target cancer cell line 100 μL, anti-human CD107a-APC (BD Pharmingen, 560664) 1 μL Well 3: Suspended NK cells 100 μL, suspended target cancer cell line 100 μL, APC mouse IgG1 k isotype control (BD Pharmingen, 555751) 5 μL The 96 well plate was wrapped by foil, and then stored in 37° C. incubator for 4 hours. After 4 hours, supernatant of 96 well plate was removed, and 100 μL FACS buffer, 7-AAD (BD, 559925) 5 μL, anti-human CD3-PerCP-Cy5.5 (eBioscience, 45-0036-42) 1 μL and anti-human CD56-APC-eFluor780 (eBioscience, 47-0567-42) 1 μL was added to each well.

The 96-well plate was stained by storing for 30 minutes in 4° C., and then 200 μL FACS buffer was added and centrifuged (2000 rpm) for 3 minutes (2 times).

Supernatant of 96 well plate was removed, and 200 μL of Cytofix/Cytoperm (BD, 51-20901(Z) was added to each well. Mixture in each well was well mixed by pipetting, and then was stored in 4° C. (for 30 minutes to fix).

After fixing, 200 μL of Perm/Wash buffer (BD, 51-20901 (Z) which was diluted 10 times by distilled water was added to each well and the 96-well plate was centrifuged (2000 rpm) for 3 minutes (2 times).

A set of Antibodies forth below was added after removing supernatant.

Well 1 & 2: diluted Perm/Wash 100 μL, anti-human IFN-g-FITC (BD, 554700) 1 μL, anti-human TNF-a-PE-Cy7 (eBioscience, 25-7349-82) 1 μL Well 3: diluted Perm/Wash 100 μL, FITC mouse IgG1 k isotype control (BD, 555748) 5 μL, PE-Cy7 mouse IgG1 k isotype control (BD, 557872) 5 μL Cytokine was stained by storing the 96-well plate for 30 minutes in 4° C. After staining, 200 μL of Perm/Wash buffer (BD, 51-20901(Z) which was diluted 10 times by distilled water was added to each well and the 96-well plate was centrifuged (2000 rpm) for 3 minutes (2 times).

Finally, each well was resuspended by adding 200 μL of diluted Perm/Wash buffer (BD, 51-20901(Z), the ability of cytokine secretion was evaluated by FACS-Fortessa (BD).

Figure 15:
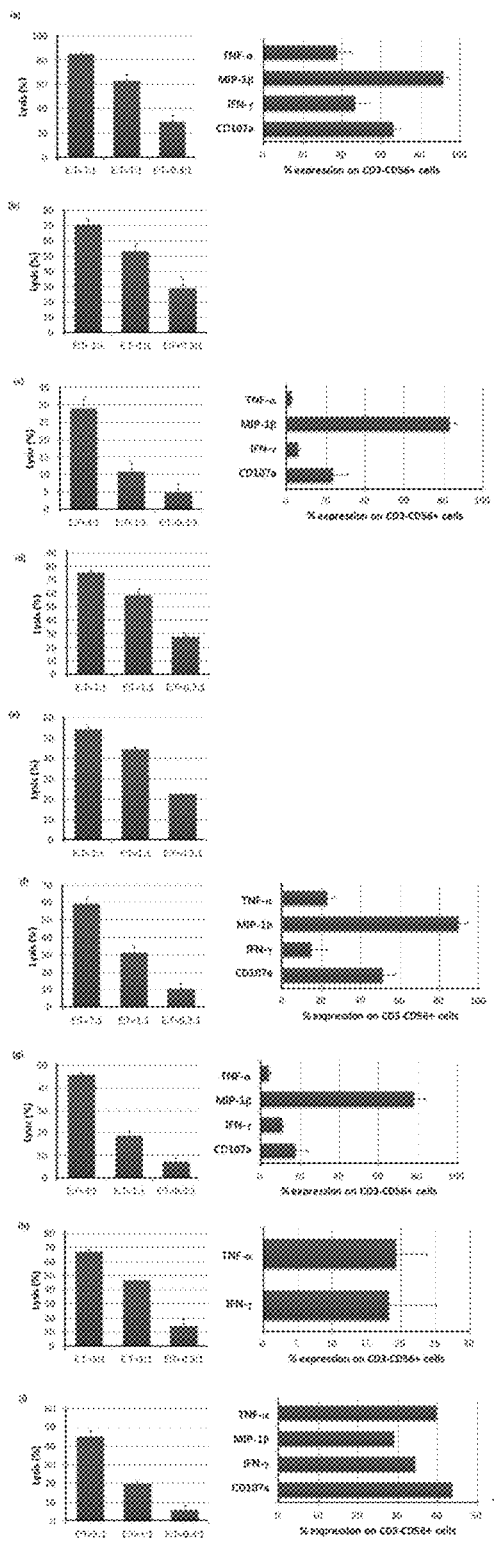
FIG. 15 shows the in-vitro efficacy of NK cells against various cancer cell lines and virus infected cell lines.
  (a) cell cytotoxicity and secretion ability of cytokine against K562 cell lines (Leukemia)
  (b) cell cytotoxicity against Raji cell lines (Lymphoma)
  (c) cell cytotoxicity and secretion ability of cytokine against SK-N-SH cell lines (Neuroblastoma)
  (d) cell cytotoxicity against SNUOT-Rb1 cell lines (Retinoblastoma)
  (e) cell cytotoxicity against U87-MG cell line (Glioblastoma)
  (f) cell cytotoxicity and secretion ability of cytokine against OVCAR-3 cell lines (ovarian cancer)
  (g) cell cytotoxicity and secretion ability of cytokine against Huh-7 cell lines (HCC, Hepatocellular carcinoma), (h) cell cytotoxicity and secretion ability of cytokine against SNU398 cell lines (HBV infected HCC)
  (i) cell cytotoxicity and secretion ability of cytokine against Huh-7.5 cell lines (HCV infected HCC)

FIG. 15 shows the in-vitro efficacy (cytotoxicity and ability of cytokine secretion) of NK cells on various cancer cell lines and virus infected cell lines as follows;

(a) K562 cell lines (Leukemia)
(b) Rajj cell lines (Lymphoma)
(c) SK-N-SH cell lines (Neuroblastoma)
(d) SNUOT-Rb1 cell lines (Retinoblastoma)
(e) U87-MG cell line (Glioblastoma)
(f) OVCAR-3 cell lines (ovarian cancer)
(g) Huh-7 cell lines (HCC, Hepatocellular carcinoma)
(h) SNU398 cell lines (HBV infected HCC)
(i) Huh-7.5 cell lines (HCV infected HCC)

NK cells showed excellent cell cytotoxicity to most of cancer cell lines. Moreover, NK cells showed good cytotoxicity to virus infected cell lines.

The ability of cytokines secretion of NK cells was observed in some cell line, especially, NK cells showed the strong cytokine secretion ability against K562 cell lines and virus infected cancer cell lines (HBV and HCV infected HCC cell lines).

In conclusion, it is confirmed that NK cells produced according to the present invention have an excellent efficacy (cytotoxicity and ability of cytokine secretion) against various cancer cell lines and virus infected cell lines.

INDUSTRIAL APPLICABILITY

As described above, when the NK cell culture technology is used, that is, when NK cells are produced by performing stationary culture in a medium containing anti-CD3 antibody and cytokine while repeated stimulation with feeder cells is performed, followed by suspension culture, NK cells having high purity, high cytotoxicity and high cell viability can be highly efficiently produced by a clinically friendly method compared to a conventional method. NK cells produced by the method of the present invention have excellent long-term storage stability, because the cell viability and cytotoxicity thereof can be stably maintained over a long period of time.

Particularly, when albumin is added to a composition containing the NK cells produced by the method of the present invention, the cytotoxicity and cell viability can be greatly increased. Also, due to the characteristics of the production method of the present invention, the cytotoxicity (i.e., therapeutic effect) and cell viability of the NK cells can be maintained even when they are thawed after frozen. Thus, the NK cells can be easily stored and supplied in a liquid or frozen state without needing an additional treatment process.

The NK cells produced by the present invention can stably exhibit their effect in vivo, and thus a composition containing the same as an active ingredient can be effectively used for treatment of cancers and infectious diseases.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for producing NK cells, comprising the steps of: (i) isolating peripheral blood leukocytes and NK cells from human peripheral blood; (ii) carrying out stationary culture of NK cells for 2-15 days in a medium containing anti-CD3 antibody, cytokine and inactivated peripheral blood mononuclear cells (PBMCs) as feeder cells to stimulate by cell-cell contact; (iii) after completion of stationary culture in step (ii), re-stimulating the cells by addition of cytokine, anti-CD3 antibody and inactivated peripheral blood mononuclear cells (PBMCs) as feeder cells, (iv) carrying out stationary culture for 2-7 days to stimulate cause cell-cell contact; (v) after completion of the stationary culture, adding to the cells a medium containing cytokine required for stationary or suspension culture, and carrying out stationary or suspension culture while maintaining cell concentration and cytokine concentration at constant levels.

2. The method of claim 1, wherein step (iii) of re-stimulating the cells and carrying out stationary culture is repeated twice or more.

3. The method of claim 1, wherein the suspension culture in step (v) is performed by using a reactor selected from the group consisting of a shaking flask, a shaking incubator, a fermentor, a T-flask, and a disposable cell culture bag.

4. The method of claim 1, wherein the stationary culture in step (ii) or (iii) and the stationary or suspension culture in step (v) are performed in a same or different reactor.

5. The method of claim 1, the concentrations of cell and cytokine in the medium are measured during the stationary or suspension culture in step (v), and the medium containing cytokine are added in order to maintain cell and cytokine concentration at constant levels.

6. The method of claim 1, wherein the anti-CD3 antibody is one or more selected from the group consisting of OKT3, UCHT1, and HIT3a.

7. The method of claim 6, wherein the anti-CD3 antibody is OKT-3 antibody.

8. The method of claim 1, wherein the cytokine is one or more selected from the group consisting of interleukin-2 (IL-2), interleukin-12 (IL-12), interleukin-15 (IL-15), interleukin-18 (IL-18), and interleukin-21 (IL-21).

9. The method of claim 8, wherein the cytokine is IL-2.

* * * * *